(12) United States Patent
Helmer

(10) Patent No.: US 11,179,544 B2
(45) Date of Patent: Nov. 23, 2021

(54) CATHETER FOR TAVR PROCEDURES

(71) Applicant: NorMedix, Inc., Eden Prairie, MN (US)

(72) Inventor: Gregory Helmer, Excelsior, MN (US)

(73) Assignee: NorMedix, Inc., Eden Prairie, MN (US)

( * ) Notice: Subject to any disclaimer, the term of this patent is extended or adjusted under 35 U.S.C. 154(b) by 217 days.

(21) Appl. No.: 15/521,579

(22) PCT Filed: Oct. 23, 2015

(86) PCT No.: PCT/US2015/057147
§ 371 (c)(1),
(2) Date: Apr. 24, 2017

(87) PCT Pub. No.: WO2016/065278
PCT Pub. Date: Apr. 28, 2016

(65) Prior Publication Data
US 2018/0200477 A1    Jul. 19, 2018

Related U.S. Application Data

(60) Provisional application No. 62/068,403, filed on Oct. 24, 2014.

(51) Int. Cl.
*A61M 25/00* (2006.01)
*A61M 31/00* (2006.01)
(Continued)

(52) U.S. Cl.
CPC ...... *A61M 25/007* (2013.01); *A61M 25/0041* (2013.01); *A61M 31/005* (2013.01); *A61F 2/2427* (2013.01); *A61M 2025/0163* (2013.01)

(58) Field of Classification Search
CPC ............. A61M 31/005; A61M 25/007; A61M 25/0041; A61M 2210/125;
(Continued)

(56) References Cited

U.S. PATENT DOCUMENTS 4,169,464 A    10/1979    Obrez
4,694,838 A *   9/1987    Wijayarthna ......... A61M 5/007
                                                  600/435

(Continued)

FOREIGN PATENT DOCUMENTS

JP    60190968 A    9/1985
JP    11244391 A    9/1999
(Continued)

OTHER PUBLICATIONS

"European Application Serial No. 15852982.6, Response filed Sep. 24, 2018 to Extended European Search Report dated Feb. 23, 2018", 9 pgs.

(Continued)

*Primary Examiner* — Lauren P Farrar
*Assistant Examiner* — Hamza A Darb
(74) *Attorney, Agent, or Firm* — Schwegman Lundberg & Woessner, P.A.

(57) ABSTRACT

Embodiments of the invention include a single lumen catheter for delivering high pressure contrast injection for TAVR procedures. The catheter comprises a main lumen for delivering contrast media extending from the proximal end to the distal pigtail end, a distal end hole for delivering contrast media, one or more side holes proximate of the end hole along the catheter shaft on the distal angled portion, a distal angled section that is angled from the main catheter lumen axis, a distal pigtail configuration that is angled from the axis of the distal section, and a distal pigtail loop. Other embodiments are also included herein.

27 Claims, 3 Drawing Sheets

(51) Int. Cl.
*A61F 2/24* (2006.01)
*A61M 25/01* (2006.01)

(58) Field of Classification Search
CPC .... A61M 2210/127; A61M 2025/0163; A61M 25/003; A61M 25/0067; A61M 25/0074; A61F 2/2427
See application file for complete search history.

(56) References Cited

U.S. PATENT DOCUMENTS

| | | | | |
|---|---|---|---|---|
| 4,747,840 | A * | 5/1988 | Ladika | A61M 25/0041 604/264 |
| 5,163,928 | A | 11/1992 | Hobbs et al. | |
| 6,280,434 | B1 * | 8/2001 | Kinoshita | A61M 25/0041 600/435 |
| 2006/0258978 | A1 | 11/2006 | Vanney | |
| 2014/0155994 | A1 | 6/2014 | Mcdonald | |

FOREIGN PATENT DOCUMENTS

| | | |
|---|---|---|
| JP | 2002186670 A | 7/2002 |
| JP | 2004267496 A | 9/2004 |
| JP | 2005095552 A | 4/2005 |
| JP | 3151538 U | 6/2009 |
| JP | 2018502673 A | 2/2018 |
| JP | 6785232 | 10/2020 |
| WO | WO-2011015218 A1 | 2/2011 |

OTHER PUBLICATIONS

"International Application Serial No. PCT/US2015/057147, International Preliminary Report on Patentability dated May 4, 2017", 6 pgs.

"International Application Serial No. PCT/US2015/057147, International Search Report dated Jan. 28, 2016", 3 pgs.

"International Application Serial No. PCT/US2015/057147, Written Opinion dated Jan. 28, 2016", 4 pgs.

"European Application Serial No. 15852982.6, Extended European Search Report dated Feb. 23, 2018", 10 pgs.

"European Application Serial No. 15852982.6, Response filed Dec. 19, 2017 to Communication pursuant to Rules 161(2) and 162 EPC dated Jun. 9, 2017", 4 pgs.

"Japanese Application Serial No. 2017-540975, Office Action dated Aug. 20, 2019", w/ English translation, 8 pgs.

"Japanese Application Serial No. 2017-540975, Response filed Feb. 20, 2020 to Office Action dated Aug. 20, 2019", w/ English Claims, 4 pgs.

"Japanese Application Serial No. 2017-540975, Final Notification of Reasons for Rejection dated Jun. 2, 2020", w/ English Translation, 5 pgs.

"Japanese Application Serial No. 2017-540975, Response filed Aug. 31, 2020 to Final Notification of Reasons for Rejection dated Jun. 2, 2020", w/ English Claims, 3 pgs.

"Mexican Application Serial No. MX a 2017 005331, Response filed Jan. 19, 2021 to Office Action dated Nov. 6, 2020", with machine English translation, 27 pages.

"European Application Serial No. 15852982.6, Resposne filed Mar. 29, 2021 to Communication Pursuant to Article 94(3) EPC dated Sep. 21, 2020", 11 pages.

"European Application Serial No. 15852982.6, Communication Pursuant to Article 94(3) EPC dated Sep. 21, 2020", 5 pages.

"Mexican Application Serial No. MX a 2017 005331, Office Action dated Nov. 6, 2020", with English translation, 12 pages.

"Mexican Application Serial No. MX a 2017 005331, Office Action dated Apr. 30, 2021", with English translation, 8 pages.

"Mexican Application Serial No. MX/a/2017/005331, Response filed Aug. 10, 2021 to Office Action dated Apr. 30, 2021", w/o English claims, 16 pgs.

* cited by examiner

CATHETER FOR TAVR PROCEDURES

This application is a U.S. National Stage Filing under 35 U.S.C 371 of International Patent Application Serial No. PCT/2015/057147, filed Oct. 23, 2015, and published as WO/2016/065278 on Apr. 28, 2016, which claims priority to U.S. Provisional Patent Application No. 62/068,403, filed Oct. 24, 2014, the benefit of priority of each of which are claimed hereby and each of which are incorporated by reference herein in their entirety.

FIELD OF THE TECHNOLOGY

The present application relates to a catheter. More specifically, the present application relates to a catheter for TAVR procedures.

BACKGROUND

A transcatheter aortic valve replacement ("TAVR") can include the use of a catheter to replace a heart valve, such as the aortic valve of the heart. A TAVR procedure can be a minimally invasive surgical procedure to repair a valve in the heart without removing the old valve.

In some scenarios a diagnostic pigtail catheter for opacifying the aortic cusps can be used in the TAVR procedure. Current pigtail diagnostic catheters for coronary interventions are typically made of two designs; 1) an angled pigtail catheter for facilitation of the catheter into the left ventricle or 2) a straight pigtail catheter for general purpose use in allowing for dye opacification of larger vascular structures. Neither catheter is designed for opacification of the aortic cusps or even more specifically for ideal placement into the non-coronary cusp of the aortic valve for appropriate coaxial alignment of the stented valve during transcatheter aortic valve replacement (TAVR).

SUMMARY

Embodiments of the invention include a single lumen catheter for delivering high pressure contrast injection for TAVR procedures. The catheter comprising a main lumen for delivering contrast media extending from the proximal end to the distal pigtail end, a distal end hole for delivering contrast media, one or more side holes proximate of the end hole along the catheter shaft on the distal angled portion, a distal angled section of 2-5 cm in length that is angled at 25-45 degrees from the main catheter lumen axis, a distal pigtail configuration that is angled so its plane is 30-60 degrees from the axis of the distal section, a distal pigtail configuration that is oriented substantially 90 degrees relative to the main shaft of the catheter, and a distal pigtail loop that is 10-20 mm in diameter.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The embodiments of the present technology described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The catheter as described herein can provide a means to allow optimal chamber opacification without movement of the catheter while positioning the catheter into the non-coronary cusp.

Figure 1:
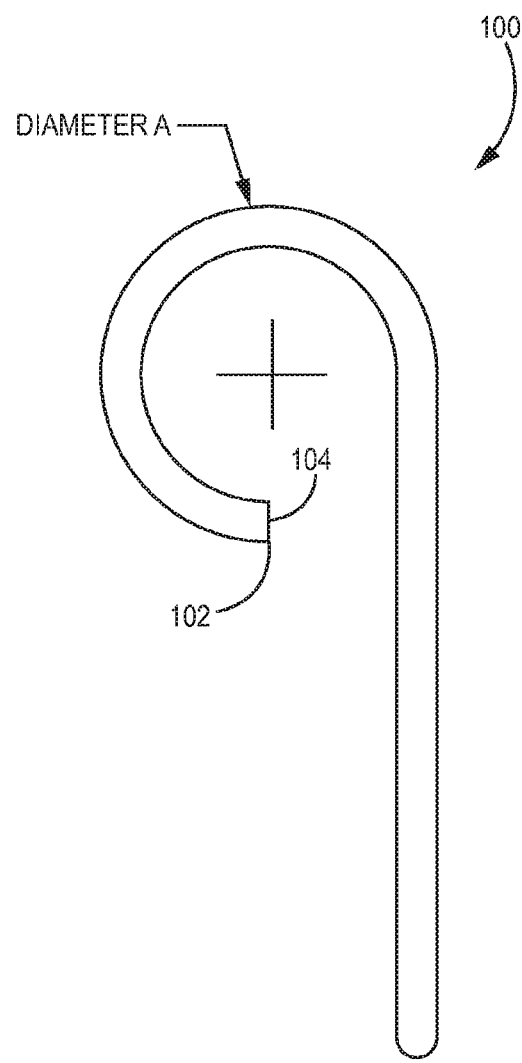
FIG. 1 is a view of an end of a catheter, according to an embodiment.

FIG. 1 shows a view of a portion of a catheter 100. The catheter 100 can include a single lumen. The catheter 100 can be configured to deliver a high pressure contrast injection, such as for a TAVR procedure. In an embodiment, the catheter 100 can include a proximal end (not shown) and a distal end 102. The proximal end of the catheter 100 can include a luer connection, such as a female luer connection. The female luer connection can be configured for adequate pressure retention during high pressure dye injections.

The distal end 102 can be a pigtail end, such that the distal end 102 can include a pigtail loop. The loop can be substantially circular, such that as when viewed from a side, such as shown in FIG. 1, the pigtail loop can define at least a portion of a circle. The loop can have a diameter, such as diameter A shown in FIG. 1. In an embodiment, the loop has a diameter of at least 10 mm and not more than 20 mm. In an embodiment, the loop has a diameter of at least 5 mm and not more than 30 mm. In an embodiment, the pigtail loop extends 360 degrees. In an alternative embodiment, the pigtail loop extends 270 degrees, such as shown in FIG. 1. In an embodiment, the pigtail loop can extend at least 90 degrees and not more than 540 degrees. In an embodiment, the pigtail loop can extend at least 270 degrees and not more than 360 degrees.

The distal end 102 can define a distal hole 104, such as a hole from the catheter that is configured to deliver the contrast media. In an embodiment, the distal hole 104 can be located at the end of the catheter 100. In an embodiment, the distal hole 104 can be a continuation of a main lumen.

The catheter 100 can include a main lumen, such as center lumen that extends from the proximal end of the catheter to the distal end 102. The main lumen can be configured to deliver a contracts media. The main lumen can have a substantially circular cross section.

The catheter 100 can include a single lumen catheter with a braid reinforced polymer shaft. The catheter 100 can include Pebax. The catheter 100 can include a stainless steel. In an embodiment, the catheter 100 can include Pebax and a stainless steel braid reinforcement. In an embodiment, the catheter 100 can be configured for contrast injection pressures of up to at least 1200 psi.

The catheter 100 can define one or more dye infusion holes. The dye infusion holes can be located at a minimum of 1 cm away from the distal tip. The dye infusion holes can be located at a maximum of 3 cm away from the distal tip. In an embodiment, the dye infusion holes can be located between 1 cm and 3 cm away from the distal tip. In an embodiment, the dye infusion holes can be located between 0.5 cm and 5 cm away from the distal tip. In an embodiment, the dye infusion holes can be located at different distances away from the distal tip.

In an embodiment, there can be at least 1 dye infusion hole. In an embodiment, there can be 5 or less dye infusion holes. In an embodiment, there can be 2, 3, or 4 dye infusion holes. In an embodiment, the pigtail distal end 102 of the catheter is not braid reinforced. In an embodiment, the portion of the catheter that defines the one or more dye infusion holes is not braid reinforced. In an embodiment, the braid reinforcement terminates between the proximal end of the catheter and the dye infusion hole closest to the proximal end.

Figure 2:
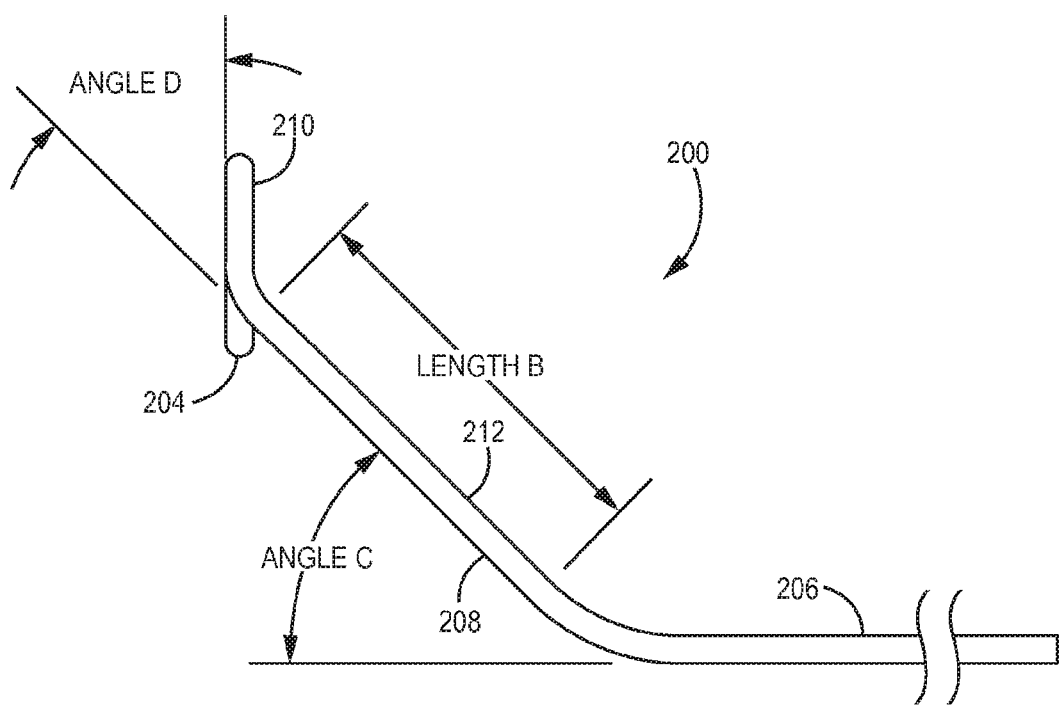
FIG. 2 is a view of a portion of a catheter, according to an embodiment.

FIG. 2 shows a view of a portion of a catheter 200, The catheter 200 can include a main shaft portion 206, a distal angled portion 208 and the pigtail loop 210. The pigtail loop 210 can define the distal end hole 204, The distal end hole 204 can be configured to deliver contrast media. As shown in FIG. 2 a plane of the pigtail loop 210 extends into and out of the page and is accordingly transverse to a plane including both the distal main shaft portion 206 and the distal angled portion 208.

The distal angled portion 208 can define one or more dye infusion holes 212. In an embodiment, the distal angled portion can be at least 2 cm long and not longer than 5 cm, such as shown by length B in FIG. 2. Alternative ranges for the length of the distal angled portion 208 are also possible, such as lens to 6 cm, or 2 cm to 8 cm. The distal angled portion 208 can angled from the main shaft portion 206, such as represented by angle C in FIG. 2. The distal angled portion 208 can be angled from the main shaft portion 206 by at least 25 degrees and not more than 45 degrees. In an alternative embodiment, the distal angled portion 208 is angled at least 15 degrees and not more than 60 degrees from the main shaft portion 206.

The distal pigtail loop 210 can be angled from distal angled portion 208, such as represented by angle D in FIG. 2, The distal pigtail loop 210 can be angled from distal angled portion 208, such as by at least 30 degrees and not more than 60 degrees. In an alternative embodiment, the distal pigtail loop 210 can be angled at least 20 degrees and not more than 90 degrees from the distal angled portion 208.

The distal pigtail loop 210 can be configured such that it is about 90 degrees relative to the main shaft portion 206. In some embodiments, the distal pigtail loop 210 can be angled from the main shaft portion 206 by at least 60 degrees and not more than 120 degrees.

Figure 3:
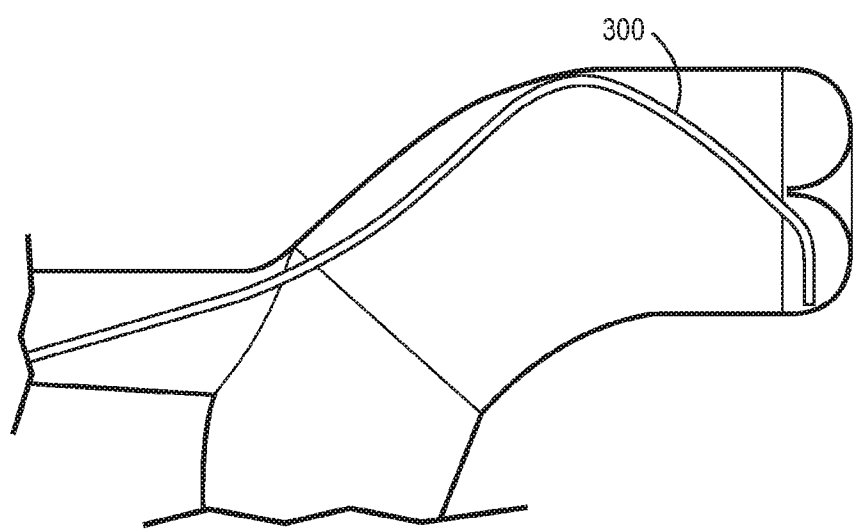
FIG. 3 is a view of a portion of a catheter and a portion of an environment in which it can be used, according to an embodiment.

FIG. 3 shows a view of a portion of a catheter 300 and a portion of an environment in which the catheter 300 can be used. In an embodiment, the catheter 300 can be a diagnostic TAVR pigtail catheter. The catheter 300 can be optimally configured to opacify the non-coronary aortic cusp. The catheter 300 can allow for chamber opacification with little movement of the catheter 300, such as while the catheter 300 is positioned in the non-coronary cusp of the aortic root. In a similar manner to FIG. 2 the pigtail loop is aligned with a plane extending into and out of the page. The pigtail loop is transverse to the proximal portions of the catheter 300, for instance including the distal main shaft portion 206 and the distal angled portion 208 shown in FIG. 2. As shown in FIG. 2 and FIG. 3 the distal main shaft portion 206 and distal angled portion 208 extend along the plane of the page and are transverse to the pigtail loop (element 210 in FIG. 2).

In some TAVR procedures, as a guidewire and catheter track around the aortic arch, the catheter can tend to lay along the greater curvature, placing the catheter into the right coronary cusp. The non-coronary cusp can lie posterior and leftward in relation to the right coronary cusp. Therefore the catheter 300 can include a left angle (causing displacement off the center line by approximately 2 cm) and an approximately 25 degree angle directed true posterior. An alternative catheter can have a similar displacement leftward (as most aortic roots are near 4 cm) and have a 40 degree angle directed posterior.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A catheter for delivering a fluid media comprising:
   a main catheter portion extending from a proximal catheter end toward a distal catheter end;
   an angled assembly coupled with the main catheter portion near the distal catheter end, the angled assembly includes:
      a pigtail loop at a first angle relative to the main catheter portion,
      a distal angled segment extending from the main catheter portion to the pigtail loop, the distal angled segment extending from the main catheter portion to the pigtail loop at a second angle relative to the main catheter portion, and
   wherein the pigtail loop extends from the distal angled segment at a third angle relative to the distal angled segment, and a plane of the pigtail loop is transverse to a plane including the main catheter portion and the distal angled segment; and wherein the pigtail loop includes at least one fluid media hole and the distal angled segment includes fluid media holes configured for dispensing a fluid media.

2. The catheter of claim 1, wherein the distal angled segment is straight between the main catheter portion and the pigtail loop.

3. The catheter of claim 1, wherein the angled assembly includes a non-coronary cusp configuration, the non-coronary cusp configuration includes:
   a distal angled joint between the main catheter portion and the distal angled segment, the distal angled joint configured for engagement along a greater curvature of an aortic arch, and
   a pigtail joint between the distal angled segment and the pigtail loop, the pigtail joint configured to cooperate with the distal angled joint and the distal angled segment and position the pigtail loop at the non-coronary cusp.

4. The catheter of claim 3, wherein in the non-coronary cusp configuration the distal angled segment is configured to span the aortic arch from the distal angled joint proximate the greater curvature to the pigtail joint proximate the non-coronary cusp.

5. The catheter of claim 1, wherein the angled assembly includes a non-coronary cusp configuration, and in the non-coronary cusp configuration the distal angled segment is configured to span an aortic arch from a greater curvature of the aortic arch to proximate a non-coronary cusp.

6. The catheter of claim 1, wherein the main catheter portion includes a main lumen extending from the proximal catheter end toward the distal catheter end.

7. The catheter of claim 6, wherein the main lumen extends from the main catheter portion into the distal angled segment, and the main lumen is in communication with at least one fluid media hole of the fluid media holes in the distal angled segment configured for dispensing the fluid media.

8. The catheter of claim 7, wherein the main lumen extends from the distal angled segment into the pigtail loop, and the main lumen is in communication with at least one fluid media hole of the fluid media holes in the pigtail loop and the distal angled segment configured for dispensing the fluid media.

9. The catheter of claim 1, wherein the at least one fluid media hole includes a distal end hole in the pigtail loop.

10. The catheter of claim 1, wherein the distal angled segment is 2 to 5 centimeters in length and the second angle is between 25 to 45 degrees relative to an axis of the main catheter portion.

11. The catheter of claim 1, wherein the pigtail loop is 10 to 20 millimeters in diameter and the first angle is about 90 degrees relative to an axis of the main catheter portion.

12. The catheter of claim 1, wherein the third angle of the pigtail loop is between 30 to 60 degrees relative to an axis of the distal angled segment.

13. A catheter for delivering a fluid media comprising:
   a main catheter portion extending from a proximal catheter end toward a distal catheter end;
   an angled assembly coupled with the main catheter portion near the distal catheter end, the angled assembly includes:
      a distal angled segment,
      a pigtail loop, and the pigtail loop includes at least one fluid media hole and the distal angled segment includes fluid media holes,
      a distal angled joint between the main catheter portion and the distal angled segment,
      a pigtail joint between the distal angled segment and the pigtail loop,
   wherein the distal angled segment extends from the distal angled joint to the pigtail joint at a segment angle relative to the main catheter portion, the segment angle imparted by the distal angled joint, and
   wherein the pigtail loop is transverse to a plane including the main catheter portion and the distal angled segment; and
   wherein the angled assembly includes a non-coronary cusp configuration, and in the non-coronary cusp configuration the distal angled segment is configured to span an aortic arch from the distal angled joint proximate a greater curvature of the aortic arch to the pigtail joint proximate a non-coronary cusp.

14. The catheter of claim 13, wherein the distal angled joint is configured for engagement along the greater curvature of the aortic arch in the non-coronary cusp configuration.

15. The catheter of claim 13, wherein in the non-coronary cusp configuration the pigtail joint is configured to cooperate with the distal angled joint and the distal angled segment to position the pigtail loop at the non-coronary cusp.

16. The catheter of claim 13, wherein the at least one fluid media hole of the pigtail loop includes a plurality of fluid media holes.

17. The catheter of claim 13, wherein the at least one fluid media hole includes a distal end hole of the pigtail loop.

18. The catheter of claim 13, wherein the distal angled segment is straight between the main catheter portion and the pigtail loop.

19. The catheter of claim 13, wherein the main catheter portion and at least one of the distal angled segment or the pigtail loop includes a main lumen in communication with the at least one fluid medial hole.

20. The catheter of claim 13, wherein the distal angled segment is 2 to 5 centimeters in length and is angled between 25 to 45 degrees relative to an axis of the main catheter portion.

21. The catheter of claim 13, wherein the pigtail loop is 10 to 20 millimeters in diameter and is angled about 90 degrees relative to an axis of the main catheter portion.

22. The catheter of claim 13, wherein the pigtail loop is angled between 30 to 60 degrees relative to an axis of the distal angled segment.

23. The catheter of claim 13, wherein the pigtail loop is aligned along a plane.

24. A method for use with a transcatheter aortic valve replacement comprising:
   navigating an angled assembly of a catheter for delivering a fluid media having a main catheter portion to an aortic arch; and
   positioning the angled assembly of the catheter in a non-coronary cusp configuration in the aortic arch, positioning includes:
      engaging a distal angled joint with a greater curvature of the aortic arch, the distal angled joint between the main catheter portion and a distal angled segment of the angled assembly,
      positioning a pigtail loop of the angled assembly proximate a non-coronary cusp, positioning includes biasing the pigtail loop toward the non-coronary cusp with the engaged distal angled joint, the distal angled segment and a pigtail joint between the distal angled segment and the pigtail loop, wherein the distal angled segment is at second angle relative to the main catheter portion, the second angle imparted by the distal angled joint, and the pigtail loop is at a first angle relative to the main catheter portion and at a third angle relative to the distal angled segment, and a plane of the pigtail loop is transverse relative to a plane including the distal angled segment and the main catheter portion, and wherein the pigtail loop includes at least one fluid media hole and the distal angled segment includes fluid media holes configured for dispensing a fluid media.

25. The method of claim 24, wherein positioning the angled assembly of the catheter in the non-coronary cusp configuration includes spanning the aortic arch from the distal angled joint at the greater curvature to the pigtail joint and the pigtail loop proximate the non-coronary cusp.

26. The method of claim 24 comprising opacifying the non-coronary cusp with fluid media dispensed by at least one fluid media hole in one or more of the pigtail loop or the distal angled segment with the angled assembly in the non-coronary cusp configuration.

27. The method of claim 26, wherein the at least one fluid media hole includes a distal end hole of the pigtail loop, and opacifying the non-coronary cusp includes dispensing fluid media from the distal end hole of the pigtail loop with the pigtail loop proximate the non-coronary cusp.

* * * * *